US006319958B1

(12) United States Patent
Johnson et al.

(10) Patent No.: US 6,319,958 B1
(45) Date of Patent: *Nov. 20, 2001

(54) METHOD OF SENSITIZING MICROBIAL CELLS TO ANTIMICROBIAL COMPOUND

(75) Inventors: Eric A. Johnson; Byron F. Brehm-Stecher, both of Madison, WI (US)

(73) Assignee: Wisconsin Alumni Research Foundation, Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/102,466

(22) Filed: Jun. 22, 1998

(51) Int. Cl.[7] ............................. A01N 31/00; C07C 35/00
(52) U.S. Cl. ........................ 514/739; 514/675; 514/724; 568/875
(58) Field of Search .................................. 514/675, 724, 514/739; 568/875

(56) References Cited

U.S. PATENT DOCUMENTS

| 4,560,553 | 12/1985 | Zupan | 424/78 |
|---|---|---|---|
| 5,082,656 | 1/1992 | Hui et al. | 514/24 |
| 5,338,758 | 8/1994 | Chu et al. | 514/468 |
| 5,453,276 | 9/1995 | Nakatsu et al. | 424/405 |
| 5,610,196 | 3/1997 | Wood | 514/675 |

FOREIGN PATENT DOCUMENTS

| 1120820 | 3/1982 | (CA) . |
|---|---|---|
| 19631037 A1 | 2/1998 | (DE) . |
| 0 420 630 A2 | 4/1991 | (EP) . |
| 2 697 133 | 4/1994 | (FR) . |
| 61033129 | * 2/1986 | (JP) . |
| WO 92/06700 | 4/1992 | (WO) . |
| WO 93/17558 | 9/1993 | (WO) . |
| WO 96/16548 | 6/1996 | (WO) . |
| WO 97/00609 | 1/1997 | (WO) . |
| WO 98/56395 | 12/1998 | (WO) . |

OTHER PUBLICATIONS

Kadir, R. et al. Int. J. Pharmaceutics, 70, 87–94, Jan. 1991.*
Kubo, I. and Taniguchi, M., "Polygodial, an antifungal potentiator," *J. Nat. Prod.* 51(1)22–29, 1988 (Database Medline) (Abstract).
M. Bard, et al., "Geraniol Interferes with Membrane Functions in Strains of *Candida* and *Saccharomyces*," *Lipids* 23(6):534–538, 1988.
O.P. Bondar, et al., "Effects of Farnesol on the Thermotropic Behavior of Dimyristoylphosphatidylcholine," *Chem. Phys. Lipids* 74:93–98, 1994.
P.A. Cornwell and B.W. Barry, "Sesquiterpene Components of Volatile Oils as Skin Penetration Enhancers for the Hydrophilic Permeant 5–Fluorouracil," *Pharm. Pharmacol.* pp. 261–269, 1993.

(List continued on next page.)

Primary Examiner—Michael P. Woodward
Assistant Examiner—Michael Borin
(74) Attorney, Agent, or Firm—Quarles & Brady LLP

(57) ABSTRACT

A method of promoting the uptake of exogenous antimicrobial compounds by microbial cells is disclosed. In one embodiment, the method comprises the step of exposing the microbial cell to an amount of at least one sesquiterpenoid effective to enhance antimicrobial compound uptake in a microorganism and an antimicrobial compound. An antimicrobial composition comprising at least one sesquiterpenoid and an antimicrobial compound, the sesquiterpenoid being present in a concentration of between 0.1 mM and 50 mM, is also disclosed.

5 Claims, 4 Drawing Sheets farnesol (CAS #4602-84-0)

nerolidol (CAS #7212-44-4)

bisabolol (CAS #515-69-5)

apritone (CAS #68133-79-9)

OTHER PUBLICATIONS

P.A. Cornwell, et al., "Modes of Action of Terpene Penetration Enhancers in Human Skin; Differential Scanning Calorimetry, Small–Angle X–ray Diffraction and Enhancer Uptake Studies," *Int. J. Pharm.* 127:9–26, 1996.

H.G. Cutler, et al., "Antimicrobial, Insecticidal, and Medicinal Properties and Natural Product Flavors and Fragrances," *Am. Chem. Soc.* pp. 51–66, 1996.

S.D. Elakovich, "Sesquiterpenes as Phytoalexins and Allelopathic Agents," *Am. Chem. Soc.* pp. 93–108, 1997.

J. Kim, et al., "Antibacterial Activity of Some Essential Oil Components against Five Foodborne Pathogens," *J. Agric. Food Chem.* 43(11):2839–2845, 1995.

M. Knobloch, et al., "Mode of Action of Essential Oil Components on Whole Cells of Bacteria and Fungi in Plate Tests," *Bioflavour* pp. 287–299, 1988.

A.C. Williams and B.W. Barry, "Skin Absorption Enhancers," *Crit. Rev. Therap. Drug Carr. Sys.* 9(3,4):305–353, 1992.

G.L. Xiong, et al., "Effects of Penetration Enhancers on In Vitro Percutaneous Absorption of Low Molecular Weight Heparin Through Human Skin," *J. Contr. Rel.* 42:289–296, 1996.

M.A. Yamane, et al., "Terpene Penetration Enhancers in Propylene Glycol/Water Co–solvent Systems: Effectiveness and Mechanism of Action," *J. Pharm. Pharmacol.* 47:978–989, 1995.

M.A. Yamane, et al., "Effects of Terpenes and Oleic Acid as Skin Penetration Enhancers Towards 5–fluorouracil as Assessed with Time; Permeation, Partitioning and Differential Scanning Calorimetry," *Int. J. Pharm.* 116:237–251, 1995.

* cited by examiner farnesol (CAS #4602-84-0)

nerolidol (CAS #7212-44-4)

bisabolol (CAS #515-69-5)

apritone (CAS #68133-79-9)

METHOD OF SENSITIZING MICROBIAL CELLS TO ANTIMICROBIAL COMPOUND

STATEMENT REGARDING FEDERALLY SPONSORED RESEARCH OR DEVELOPMENT

This invention was made with United States government support awarded by the following agencies: USDA AGRICCREE Nos: 94-37201-1026; 96-35201-3272. The United States has certain rights in this invention.

CROSS-REFERENCE TO RELATED APPLICATION

Not applicable.

BACKGROUND OF THE INVENTION

Microbial Resistance

Increasing incidence of microbial resistance to antibiotics and other antimicrobials is a growing concern facing the medical, food and sanitation industries. Major mechanisms of microbial resistance include active drug efflux systems and mutations which lead to nonspecific decreases in cell permeability. Other routes to resistance include antimicrobial degradation, inactivation by enzymatic modifications, or alteration of the drug's target within the cell (Nikkaido, 1994).

To counter the increasing incidence of antimicrobial resistance, the pharmaceutical and other industries have invested substantial resources in the search for new inhibitory compounds of microbial, plant and animal origin. Newer strategies to overcome antimicrobial resistance have included increased production of new synthetic and semi-synthetic antibiotics which are resistant to the activities of those microbial enzymes (i.e. β-lactamases) capable of degradation or modification of naturally-derived antibiotics (Nikkaido, 1994).

Although many specific mechanisms of microbial resistance have been successfully addressed, it is thought that the more general mechanisms of altered permeability and increased efflux capability will become increasingly important from a clinical perspective (Nikkaido, 1994).

Efflux systems and mechanisms of antibiotic degradation rely on saturable biological structures (i.e., pumps or enzymes). If the nonspecific influx of an intracellularly or membrane-targeted lethal agent is high enough to overcome these inactivation mechanisms, then the effect of these mechanisms might be minimized, leading to the death of the cell.

Terpenoids

Terpenoids, a broad class of lipophilic secondary metabolites derived from mevalonate and isopentenyl pyrophosphate, occur widely in nature and have been of historical interest to man primarily for their contribution to the characteristic flavors and aromas of herbs, spices and flowers. As of 1991, the number of recognized natural terpenoids had reached an estimated 15,000 to 20,000 (Harborne, 1991).

Sesquiterpenoid compounds, containing 15 carbons, are formed biosynthetically from three 5-carbon isoprene units. Because of their naturally pleasing odors and flavors, many sesquiterpenoids of plant origin have found use in perfumery and flavoring applications and are now produced industrially from monoterpenoid feedstock. For example, nerolidol, commonly used to provide a base note for floral aroma compositions, is readily produced from linalool, itself derived from α-pinene, which occurs in high concentration in turpentine oil (Bauer, et al., 1997).

Apart from their use in perfumery, terpenoids have been associated with a variety of important biological functions as pheromones, insect antifeedants, phytoalexins and others (Harborne, 1991).

BRIEF SUMMARY OF THE INVENTION

In one embodiment, the present invention is a method of promoting the uptake of exogenous antimicrobial compounds by microbial cells. The method comprises the step of exposing the microbial cell to an amount of a sesquiterpenoid effective to enhance antimicrobial compound uptake in the microorganism and an antimicrobial compound. In a preferred embodiment of the present invention the antimicrobial compound is an antibiotic. Most preferably, the antibiotic is selected from the group consisting of clindamycin, ciprofloxacin, erythromycin, tetracycline, gentamicin, vancomycin and polymyxin B sulfate.

In one embodiment of the present invention, the method involves a topical application of the sesquiterpenoid and antimicrobial compound to human or animal skin. For example, one might apply a cream or ointment comprising the sesquiterpenoid and antimicrobial compound to a wound.

In another embodiment, the present invention is the application of the sesquiterpenoid and antimicrobial compound to a hard or soft surface, such as a food, sink, sponge or bathroom fixture.

In a preferred embodiment of the present invention, the sesquiterpenoid is selected from the group consisting of farnesol, nerolidol, bisabolol and apritone. In a most preferred form of the invention, the sesquiterpenoid is either nerolidol or farnesol.

In one form of the present invention, the sesquiterpenoid is a mixture of different sesquiterpenoids.

The present invention is also an antimicrobial compound comprising an effective amount of a sesquiterpenoid and an antimicrobial compound. In a preferred form of this embodiment of the present invention, the antimicrobial compound is an antibiotic or food grade antimicrobial.

It is an object of the present invention to provide a method of sensitizing microorganisms, such as bacteria and fungi, to antimicrobials. By means of the present invention, microorganisms will become sensitive to an antibiotic or other antimicrobial compound at dosages previously thought to be ineffective.

Other advantages, features and objects of the present invention will become apparent after one has reviewed the specification, claims and drawings.

BRIEF DESCRIPTION OF THE DRAWINGS

FIG. 3A depicts cells treated with 0.5 mM nerolidol at time 0. FIG. 3B depicts cells treated with 0.5 mM nerolidol at 5 minutes.

DETAILED DESCRIPTION OF THE INVENTION

The present invention is a method of promoting the enhanced uptake of exogenous antimicrobial compounds, including antibiotics, by cells of bacteria and fungi. The method comprises the step of exposing the microorganism to a mixture comprising a sesquiterpenoid and the antimicrobial compound. In a preferred embodiment of the present invention, one would apply a composition comprising an amount of sesquiterpenoid sufficient to increase microorganism permeability combined with an antibiotic.

In the presence of the sesquiterpenoid, microorganisms are inhibited by lower doses of antimicrobial agents or antibiotics. Thus, the present invention increases the efficacy of antimicrobial agents.

The amount of sesquiterpenoid effective for enhancing the uptake of exogenous antimicrobials can vary over a wide range. Preferably, an amount of between 0.1 mM and 50 mM would effectively facilitate antimicrobial compound uptake. Most preferably, the amount would be between 0.5 mM and 2 mM.

Figure 1:
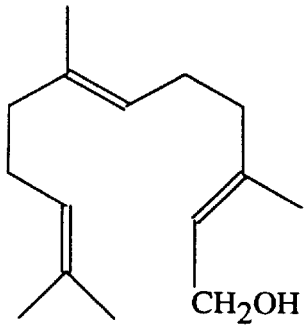
FIG. 1 is a set of chemical structures and Chemical Abstract Service (CAS) registry numbers of farnesol, nerolidol, bisabolol and apritone.
Figure 1:
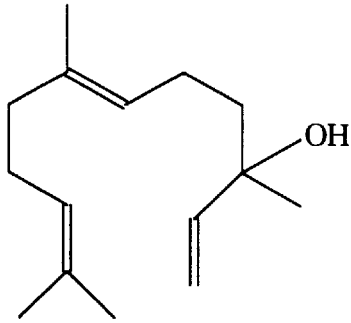
Figure 1:
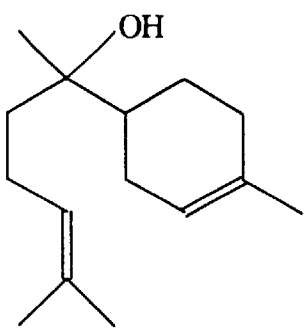
Figure 1:
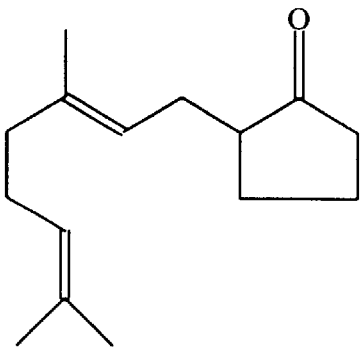

By "sesquiterpenoid" we refer to any 15-carbon compound derived from the condensation of three 5-carbon isoprene units. These compounds may be derived from natural sources (i.e., plant essential oils) or formed synthetically, may be cyclic or acyclic and may contain an oxygen atom. Preferable sesquiterpenoids include farnesol, nerolidol, bisabolol and apritone (FIG. 1). Most preferred sesquiterpenoids include farnesol and nerolidol.

Suitable antimicrobial compounds include antibiotics, preferably clindamycin, ciprofloxacin, erythromycin, tetracycline, gentamicin, vancomycin and polymyxin B sulfate. Also included are organic acids, e.g., acetic, lactic, citric, sorbic and naturally occurring hops beta-acids. Parabens and phenolics (e.g., esters of benzoic acid; p-hydroxybenzoic acid; butylated hydroxyanisole; tertiary butylhydroquinone) are also included, as are medium chain (C=8–14) fatty acids and esters, e.g., monolaurin, monocaprin, sucrose esters of fatty acids. In general, we feel that membrane active compounds (e.g., polymyxin, medium chain fatty acid esters) are most effective when combined with the sesquiterpenoids.

In one preferred embodiment, the method of the present invention requires that one expose microorganisms to a mixture comprising a sesquiterpenoid and an antimicrobial compound. However, in another embodiment either the sesquiterpenoid or the antimicrobial compound may be first exposed to the microorganism. Preferably, sesquiterpenoid is administered first.

One may also wish to include acceptable carriers and diluents in the antimicrobial composition. These carriers could include organic solvents or water. Additionally, deodorizing agents, fragrances, surfactants and buffering agents may be included.

A particularly preferred mode of administration is to a skin surface via a topical route. We envision that one may use the method and composition of the present invention to treat surface wounds or as a general antibacterial treatment. For example, one may wish to prevent sepsis or treat infections. The composition is preferably topically applied in the form of a lotion, solution, cream, ointment or powder. For treatment of sepsis or intestinal infections, oral or injectable formulations could be employed.

Additionally, the present invention will widen the antimicrobial spectra to include microorganisms not normally affected by antimicrobial agents.

For example, the composition may be formulated into a cream consisting of an aqueous emulsion of polyethylene glycols or liquid paraffin or may be incorporated at a concentration between 1 and 10% into an ointment consisting of a white wax or white soft paraffin base together with such stabilizers and preservatives as may be required. The topical compositions can contain additional ingredients such as binders, excipients, antioxidants, and dyes.

In another preferred mode of administration of the present invention, one may wish to treat hard or soft surfaces, such as tables, cutting surfaces, bathroom fixtures, showers, tubs, sponges, shower curtains, plumbing fixtures, cutlery, or sinks with a solution comprising a sesquiterpenoid and an antimicrobial compound. The composition is preferably applied in the form of a solution to be sprayed or wiped on the surface.

One may also wish to treat the surface of foods in the method of the present invention to reduce microbial growth.

Suitable target microorganisms of the present invention include both bacteria and fungi, such as yeast. Preferably, the bacteria are gram-positive bacteria.

EXAMPLES

1. In General

We have found that the sesquiterpenoids, in particular the flavorant and aroma compounds farnesol, nerolidol, bisabolol and apritone, promote the uptake of exogenous compounds, including antibiotics, by cells of gram-positive bacteria and fungi, such as yeasts. Additionally, nerolidol has been shown to dramatically increase the activity of the membrane-targeted amphiphile polymyxin B against the gram negative bacterium *Escherichia coli*.

2. Materials and Methods Chemical Reagents $\alpha$-terpinene, cineole, citral, citronellal, citronellol, ethidium bromide, farnesol, geraniol, limonene, linalool, menthone, nerolidol and terpineol were from Sigma (St. Louis, Mo.); camphene, menthone, myrcene, nerol, tetrahydrogeraniol and tetrahydrolinalool were from Aldrich (Milwaukee, Wis.); apritone and bisabolol were from Bedoukian Research, Inc. (Danbury, Conn.).

Antibiotics

Paper discs containing known quantities of clindamycin, ciprofloxacin, erythromycin, tetracycline, gentamicin and vancomycin were from Difco (BBL SensiDiscs); Polymyxin B sulfate was from Sigma (St. Louis, Mo.).

Bacterial strains and growth conditions

Erwinia sp. #351 was from Presque Isle Cultures, Presque Isle, Pa. *Lactobacillus fermentum* ATCC 14931, *Zygosaccharomyces bailii* ATCC 60483 and *E. coli* ATCC 25922 (National Committee on Clinical Laboratory Standards antibiotic test strain) were from the American Type Culture Collection, Manassas, Va. *Staphylococcus aureus* ATCC 6538 and *Enterococcus faecalis* Bact. 4025 were obtained from the UW-Madison Department of Bacteriology culture collection. All bacteria except for *L. fermentum* were grown statically in screwcap tubes containing 10 ml Trypticase Soy Broth (BBL, Cockeysville, Md.) for 20–22 hours at 30° C. *L. fermentum* was grown statically in screwcap tubes containing 10 ml MRS broth (Difco) for 20–22 hours at 30° C. Cultures of *Z. bailii* were grown in 125 ml culture flasks containing 50 ml YM broth (Difco) on a rotary shaker set at 200 rpm for 20–22 hours at 25° C.

Antibiotic Disc Assay

The activity of terpenoid compounds toward facilitating susceptibility to antibiotics was assessed using an antibiotic disc assay. For this assay, cells from an overnight growth were suspended to a known concentration in 0.5 ml 67 mM phosphate buffer, pH 7.0 and mixed with 4.5 ml 0.7% Iso-Sensitest agar (Oxoid, Basingstoke, Hampshire, England) overlay tempered to 50° C. Terpenoid compounds dissolved in absolute ethanol were added to the cell/agar overlay mixture yielding final concentrations of 0.5, 1.0 or 2.0 mM, depending on the experiment. The final concentration of ethanol in cell overlays was 0.5% and the final concentration of target cells was ca. $10^6$ cfu/ml. After thorough vortexing, terpenoid-containing cell overlays were poured over hardened Iso-Sensitest agar (2% agar) plates and allowed to set. Antibiotic discs containing clindamycin (2 μg), ciprofloxacin (5 μg), erythromycin (15 μg), tetracycline (30 μg), gentamicin (10 μg) and vancomycin (30 μg) were placed on the surface of plates containing terpenoid/cell overlays and plates were incubated at 37° C. for 22–24 hours. After incubation, zones of inhibition were measured with a ruler from the bottom of the plates.

Flow Cytometry

For experiments involving flow cytometry, overnight cultures of Erwinia sp., L. fermentum and Z. bailii were set to a concentration of ca. $10^7$ cfu/ml in 67 mM phosphate buffer, pH 7.0 (filtered, 0.2 μm). For the examination of sesquiterpenoids, cell suspensions containing either 0.5 % ethanol and 15 μM ethidium bromide or 0.5 mM apritone, bisabolol, nerolidol or farnesol dissolved in ethanol (0.5 % ethanol, final concentration) and 15 μM ethidium bromide were incubated for 40 minutes at room temperature. After incubation, cell suspensions were diluted 1:10 in 67 mM phosphate buffer, pH 7.0 (filtered, 0.2 μm) and examined using a FACScan flow cytometer (Becton Dickinson and Company, Cockeysville, Md.). Data were collected in logarithmic mode on forward scatter, side scatter and fluorescence characteristics of the cells.

Plating Assay

To assess the effect of nerolidol on enhancing polymyxin B activity against E. coli, cells from an overnight growth were suspended in 67 mM phosphate buffer to ca. $10^7$ cfu/ml and treated with either 10 ppm polymyxin B sulfate (in distilled water, filter-sterilized, 0.2 μm), 1 mM nerolidol or 10 ppm polymyxin B plus 1 mM nerolidol and incubated at 37° C. for up to 30 minutes. After incubation, cells were enumerated by pour plating in Trypticase Soy agar, tempered to 50° C. Plates were incubated overnight at 37° C. prior to counting colonies.

3. Results

Figure 2:
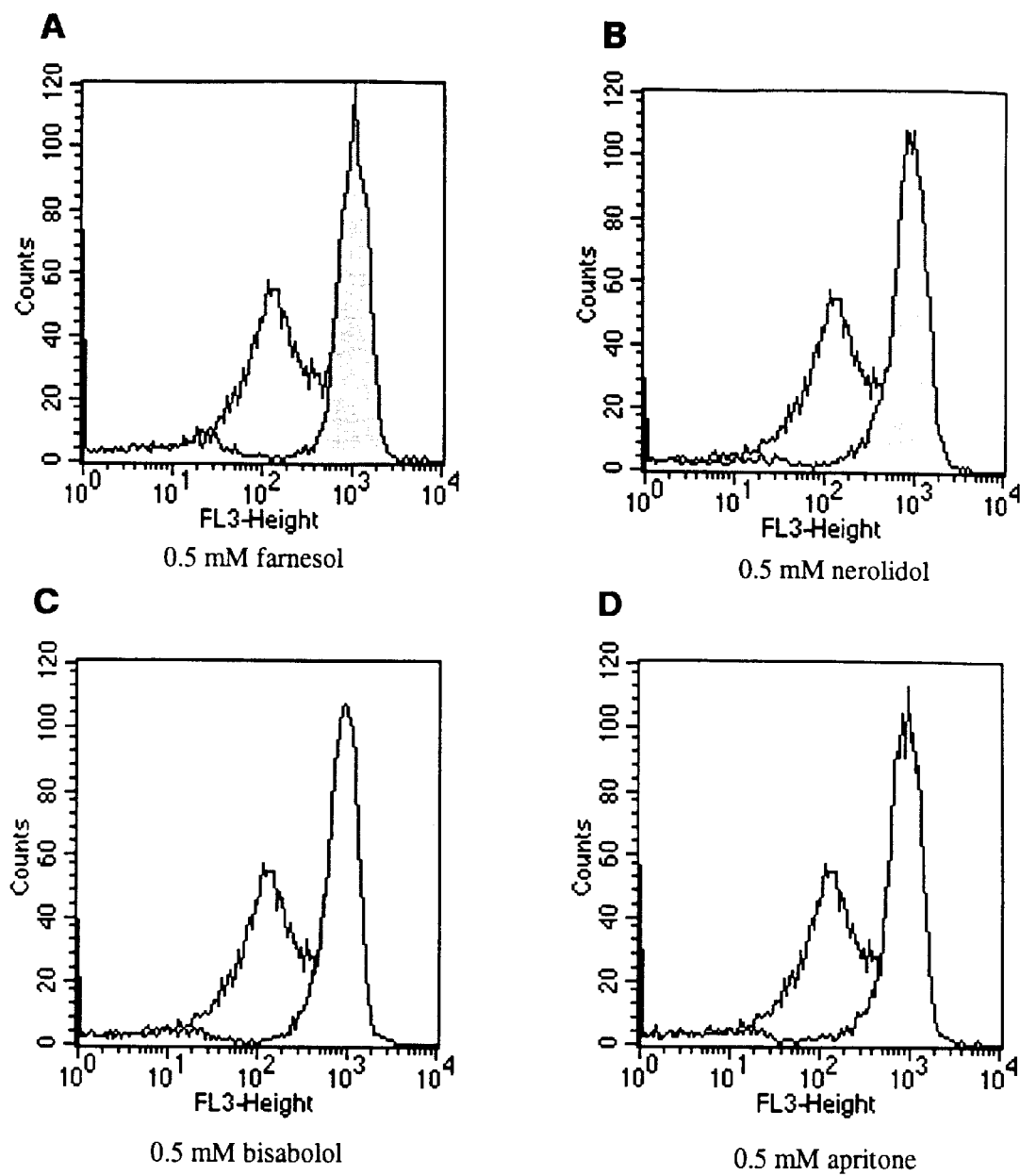
FIG. 2 is a set of four graphs depicting sesquiterpenoid-mediated uptake of ethidium bromide by cells of L. fermentum ATCC 14931. 0.5 mM farnesol was added in FIG. 2A; 0.5 mM nerolidol was added in FIG. 2B; 0.5 mM bisabolol was added in FIG. 2C; and 0.5 mM apritone was added in FIG. 2D.

A. Effects on Gram-Positive Bacteria and Yeasts: Flow cytometry demonstrated that the sesquiterpenoids apritone, bisabolol, nerolidol and farnesol facilitated the uptake of ethidium bromide by L. fermentum (FIG. 2). Farnesol led to the highest ethidium-conferred fluorescence peak, indicating the greatest degree of dye uptake.

FIG. 2 demonstrates sesquiterpenoid-mediated uptake of ethidium bromide by cells of L. fermentum ATCC 14931. Cells were treated with 15 μM ethidium bromide and 0.5 mM farnesol, nerolidol, bisabolol or apritone. Following an incubation at ambient temperatures of 40 minutes, cells were examined by flow cytometry. Rightward shift and increased height of sesquiterpenoid-treated cell populations (shaded histograms) demonstrates increased dye uptake relative to control cells treated with ethidium bromide only (non-shaded histograms).

Figure 3:
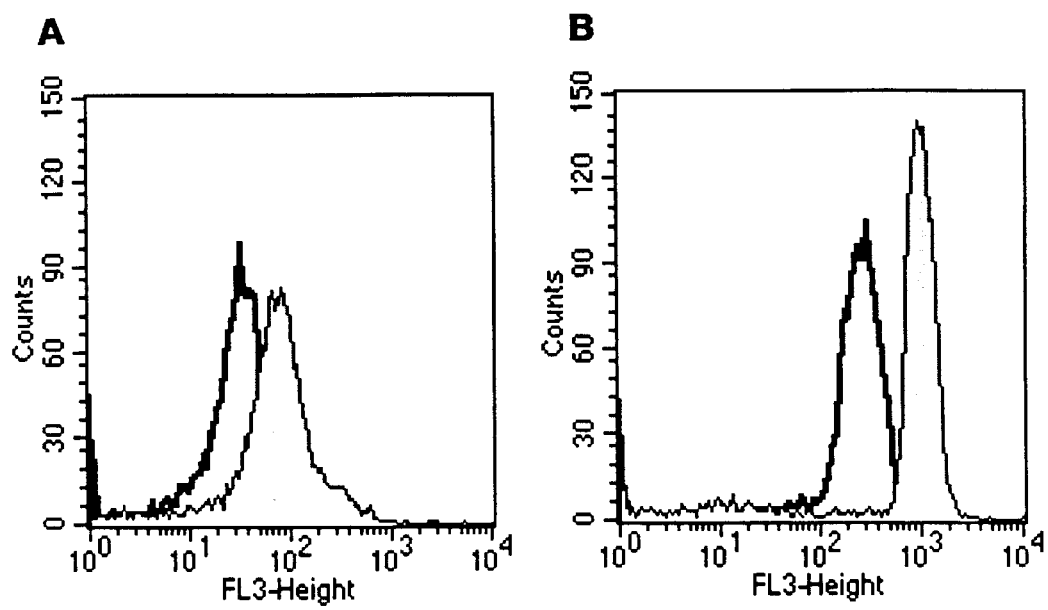
FIG. 3 is a set of two graphs depicting sesquiterpenoid-mediated uptake of ethidium bromide by cells of L. fermentum ATCC 14931.

In cells of L. fermentum treated with 0.5 mM nerolidol, substantial uptake of ethidium bromide occurred as soon as 5 minutes after ethidium and nerolidol were added to the cell suspension (FIG. 3). Sesquiterpenoid-mediated dye uptake was less pronounced for Z. bailii, with apritone leading to the greatest degree of chromosomal staining.

FIG. 3 demonstrates the rapidity of sesquiterpenoid-mediated uptake of ethidium bromide by cells of L. fermentum ATCC 14931. Cells were treated with 15 μM ethidium bromide +/−0.5 mM nerolidol and examined immediately and after 5 minutes by flow cytometry. Rightward shift and increased height of nerolidol-treated cell population (shaded histogram) demonstrates substantial dye uptake relative to control cells (non-shaded histogram) after as little as 5 minutes.

As measured by antibiotic disc diffusion assay, S. aureus demonstrated a more catholic degree of sesquiterpenoid-mediated sensitization than did E. faecalis. S. aureus was readily sensitized by apritone, bisabolol and nerolidol to six different antibiotics representing drug families of major clinical importance including the macrolide (erythromycin), aminoglycoside (gentamicin), glycopeptide (vancomycin), and fluoroquinolone (ciprofloxacin) families. The degree of sensitization depended on the amount of sesquiterpenoid present in the agar overlay, with higher sesquiterpenoid concentrations rendering S. aureus more susceptible to each antibiotic (Table 1).

TABLE 1

| Staphylococcus aureus | control | 0.5 mM | | | 1 mM | | | 2 mM | | |
| --- | --- | --- | --- | --- | --- | --- | --- | --- | --- | --- |
| | | A | B | N | A | B | N | A | B | N |
| clindamycin 2 μg | 22 | 22 | 24.5 | 23.5 | 25 | 27 | 31.5 | 27.5 | 32 | 35.5 |
| ciprofloxacin 5 μg | 21.5 | 24 | 25 | 27.5 | 24 | 30 | 30.5 | 26.5 | 30 | 34 |
| erythromycin 15 μg | 24 | 26 | 26 | 27 | 25 | 29 | 29.5 | 26.5 | 30 | 33 |
| tetracycline 30 μg | 21.5 | 25.5 | 25 | 25.5 | 26 | 26 | 26.5 | 27.5 | 30 | 32.5 |
| gentamicin 10 μg | 18.5 | 20 | 22 | 24 | 21 | 27.5 | 26 | 23 | 29 | 35 |
| vancomycin 30 μg | 18 | 19 | 20 | 20 | 18 | 19 | 23.5 | 20 | 21 | 25 |

Table 1: Effects of the sesquiterpenoids apritone (A), bisabolol (B) and nerolidol (N) on the sensitivity of S. aureus to several antibiotics. Diameters of zones of inhibition are given in millimeters. Farnesol was inhibitory at all concentrations used.

As measured by antibiotic disc diffusion assay, E. faecalis generally demonstrated only a modest degree of sensitization in the presence of 1 mM apritone, bisabolol or nerolidol. Exceptions to this modest response were with clindamycin and gentamicin. With clindamycin, zones on plates containing bisabolol and nerolidol were smaller (by 1 mm) than were control plates or those containing 1 mM apritone. With gentamicin, the presence of 1 mM nerolidol nearly doubled the size of the zone of inhibition (9 mm to 17.5 mm) (Table 2).

TABLE 2

| Enterococcus faecalis | control | 1 mM A | 1 mM B | 1 mM N |
|---|---|---|---|---|
| clindamycin 2 µg | 12 | 12 | 11 | 11 |
| ciprofloxacin 5 µg | 14 | 15.5 | 15 | 17 |
| erythromycin 15 µg | 18.5 | 18 | 19 | 19.5 |
| tetracycline 30 µg | 22 | 22.5 | 24 | 23.5 |
| gentamicin 10 µg | 9 | 11 | ND | 17.5 |
| vancomycin 30 µg | 17 | 17 | 18 | 18 |

Table 2: Effects of the sesquiterpenoids apritone (A), bisabolol (B) and nerolidol (N) on antibiotic sensitivity of *E. faecalis*. Diameters of zones of inhibition are given in millimeters. ND=not determined. Farnesol (F) was inhibitory at 1 mM.

B. Comparison of terpenoid compounds for activity, cyclic monoterpenoids, acyclic monoterpenoids and sesquiterpenoids: Because the 10-carbon monoterpenoid molecular skeleton is conserved in the 15-carbon sesquiterpenoids, and because of the lipophilic nature of terpenoid compounds as a class (Harborne, 1991), experiments were conducted to investigate whether the acyclic monoterpenoid flavorant and fragrance compounds nerol, citronellal, tetrahydrogeraniol, linalool, citronellol, geraniol and tetrahydrolinalool might also render cells competent for uptake of exogenous compounds, including antibiotics. Table 3 indicates that these compounds have weak, if any, activity with *S. aureus* and ciprofloxacin when compared with the sesquiterpenoid compounds at the same concentration (0.5 mM).

Several terpenoid flavor or aroma compounds were examined by antibiotic disc assay at a concentration of 0.5 mM for their ability to sensitize *S. aureus* to ciprofloxacin. The results are shown below in Table 3, with terpenoids grouped according to their structures as cyclic monoterpenoids, acyclic monoterpenoids or sesquiterpenoids. On plates containing cyclic monoterpenoids or acyclic monoterpenoids, measurements of zone size did not differ more than +/−1 mm relative to the control. On plates containing sesquiterpenoids, measurements of zone size varied from +2 mm to +5.5 mm relative to the control, with apritone being the least effective and nerolidol the most effective in sensitizing *S. aureus* to ciprofloxacin.

TABLE 3

| terpene | ciprofloxacin 5 µg |
|---|---|
| none | 22 |
| cyclic monoterpenoids | |
| α-terpinene | 22 |
| terpineol | 22 |
| limonene | 22 |
| camphene | 22 |
| cineole | 23 |
| menthone | 23 |
| acyclic monoterpenoids | |
| myrcene | 21.5 |
| citral | 22 |
| nerol | 22 |
| citranellal | 22 |
| tetrahydrageraniol | 22.5 |
| linalool | 22.5 |
| citronellol | 22.5 |
| geraniol | 23 |
| tetrahydralinalool | 23 |

TABLE 3-continued

| terpene | ciprofloxacin 5 µg |
|---|---|
| sesquiterpenoids | |
| apritone | 24 |
| bisabolol | 25 |
| nerolidol | 27.5 |

Table 3: Comparison of three classes of terpenoid compounds examined for the ability to sensitize *S. aureus* to antibiotic discs containing ciprofloxacin (5 µg). Terpenoid compounds are grouped as cyclic monoterpenoids, acyclic monoterpenoids and sesquiterpenoids. All terpenoid compounds were examined at a concentration of 0.5 mM.

C. Effects on Gram-Negative Bacteria: In plating experiments, nerolidol led to a dramatic increase in the susceptibility of *E. coli* to the membrane-targeted amphiphile polymyxin B (FIG. 4).

Figure 4:
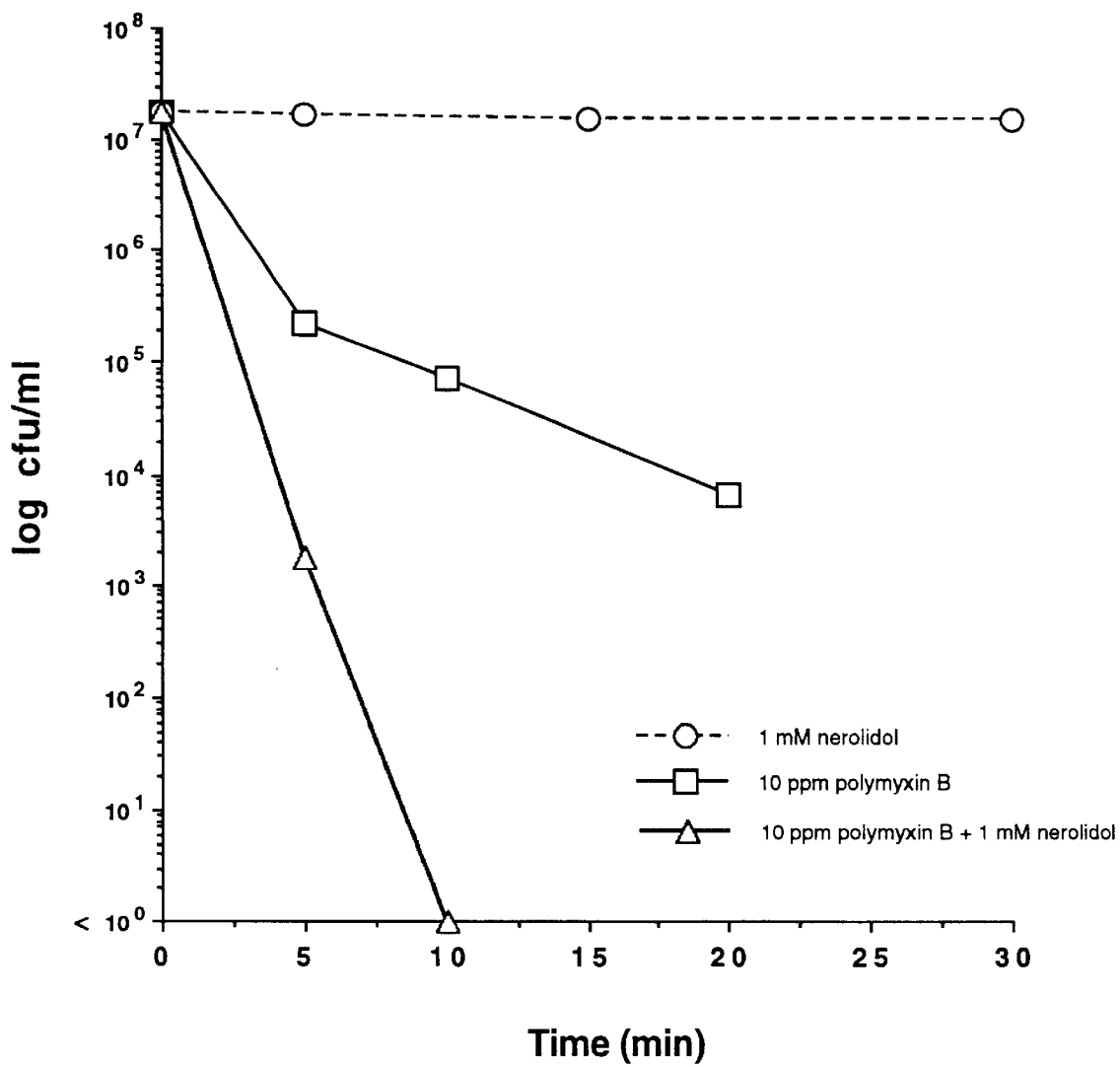
FIG. 4 is a graph (log cfu/ml by time) demonstrating the synergistic affect of nerolidol on the activity of polymixin B against E. coli ATCC 25922.

FIG. 4 demonstrates synergistic effect of nerolidol (1 mM) on activity of polymyxin B (10 ppm) against *E. coli* ATCC 25922. Cell suspensions ($1.7 \times 10^7$ cfu/ml in 67 mM phosphate buffer, pH 7.0) were treated as shown and incubated for up to 30 minutes at 37° C. Cell viability was determined at appropriate intervals by pour plating with Trypticase Soy agar tempered to 50° C.

4. Discussion

Bard, et al. studied the effects of geraniol on whole cells of yeasts and on lipid vesicles, demonstrating that geraniol increased membrane fluidity in whole cells and facilitated erythritol leakage from lipid vesicles. The most pronounced effects of geraniol on membrane fluidity were found to occur within the central (acyl chain) portion of the lipid bilayer. (Bard, et al., 1988). Bondar, et al. showed that farnesol produced similar effects on dimyristoylphosphatidylcholine (DMPC) vesicles. (Bondar, 1994).

Studies on the interactions between anesthetics or insecticides and biological membranes have correlated the presence within the bilayer of these foreign molecules with the incidence of structural defects such as mismatches in lipid packing. The macroscopic effects of these structural defects include leakiness and enhanced transmembrane permeability to a variety of solute molecules. It has been suggested as a general outcome that the presence of foreign molecules which interact with lipid acyl chains will result in increased passive bilayer permeability at temperatures away from the main lipid transition (Jorgensen, et al., 1991).

The results from our studies indicate that sesquiterpenoids such as farnesol, nerolidol, bisabolol and apritone cause the rapid and non-specific uptake of exogenous compounds, including antibiotics and food grade antimicrobials, by bacteria and fungi. The effect is most pronounced for gram-positive bacteria, presumably due to their lack of additional permeability barriers such as the outer membrane of gram negative bacteria.

We suggest that the interactions of farnesol, nerolidol, bisabolol and apritone with the cell membrane disrupt its normal function as a barrier to the passive permeation of a variety of solute molecules, including antibiotics.

Although there are literature reports regarding the ability of terpenoids to facilitate the uptake of drugs across the human stratum corneum, to our knowledge this is the first report demonstrating the use of sesquiterpenoids as a class of compounds for use in promoting the uptake of exogenous compounds across microbial lipid bilayers. It was also known that terpenoids by themselves may exert some antimicrobial activity.

To determine the ability of farnesol, nerolidol, bisabolol and apritone to permeabilize gram positive bacteria and yeasts, we used a flow cytometric assay for the uptake of ethidium bromide by *Lactobacillus fermentum* and *Zygosaccharomyces bailii*.

Ethidium bromide is a hydrophobic model drug which has limited intrinsic fluorescence and is excluded from cells with intact membranes. When cells with damaged or compromised membranes are treated with ethidium bromide, this reporter molecule is no longer excluded from the cell. Once inside the cell, ethidium bromide intercalates into double-stranded DNA and becomes highly fluorescent. Because of these properties, ethidium bromide is an excellent reporter of membrane integrity. (Midoux, 1995).

Flow cytometers are capable of analyzing thousands of cells per second on the basis of their size, granularity (cell content) and fluorescence characteristics. Briefly, cells in suspension are treated with fluorescent reporter molecules whose retention or exclusion by cells or changes in fluorescence are diagnostic of cell function. Dye-treated cells in solution are then passed individually through an intense light source (usually a laser) and data on particle size, opacity and fluorescence response of cell-bound reporter dyes is collected by a computer.

Data may be displayed in the form of histograms, dot plots, contour plots or density plots. When histograms are shown, displayed parameters are usually number of events (y-axis) vs fluorescence intensity (x-axis). This yields a fluorescence-based distribution of cells from which trends for different cellular populations may be derived. Populations of cells will shift toward the right hand side of the histogram as their fluorescence increases. If cellular fluorescence decreases, histograms will show a leftward shift.

When exposed to ethidium bromide in the presence of farnesol, nerolidol, bisabolol or apritone, cells of *L. fermentum* or *Z. bailii* became more fluorescent (seen as a rightward shift of histogram peaks) than those of the control treatment, indicating that the cell membrane is made permeable to ethidium bromide. Furthermore, cells of *L. fermentum* were made permeable as soon as 5 minutes after treatment with 0.5 mM nerolidol. These results have important implications for the rapid cellular uptake by microorganisms of other drugs sharing similar physicochemical characteristics with ethidium bromide (i.e. similar molecular weight, some degree of hydrophobicity, etc.).

The results from antibiotic disc diffusion experiments with *S. aureus* agree with data obtained by flow cytometry, showing that nerolidol, bisabolol and apritone enhance the activities of several antibiotics against this organism. Furthermore, enhancement increased as the concentration of sesquiterpenoid present in the agar overlay increased.

For the most part, results from antibiotic disc diffusion experiments were less pronounced with *E. faecalis*, an important nosocomial pathogen. However, an almost two-fold enhancement of inhibition zone size was observed when nerolidol was combined with the aminoglycoside antibiotic gentamicin against *E. faecalis*.

What makes this effect more remarkable is that enterococci are considered to be intrinsically resistant to low levels of aminoglycosides due to inefficient active cellular uptake of this class of antibiotics. (Leclercq, et al., 1992). These data support our earlier conclusions that sesquiterpenoid-mediated uptake of antibiotics is nonspecific and can therefore encompass a number of molecules. Apart from gentamicin's recognized mode of action (ribosome binding), this antibiotic has also been shown to have important membrane-destabilizing activities. This further supports our conclusion that sesquiterpenoid permeability enhancers act at the cell membrane (Kadurugamuwa, et al., 1993).

REFERENCES

1. Bard, M., Albrecht, M. R., Gupta, N., Guynn, C. and W. Stillwell, "Geraniol interferes with membrane functions in strains of Candida and Saccharomyces," *Lipids* 23(6) :534–538, 1988.
2. Bauer, K., Garbe, D. and H. Surburg, "Common fragrance and flavor materials: preparation, properties and uses," Wiley-VCH, Weinheim, 1997.
3. Bondar, O. Melnykovych, G. and E. S. Rowe, "Effects of farnesol on the thermotropic behavior of dimyristoylphosphatidylcholine," *Chem. Phys. Lipids* 74:93–98, 1994.
4. Caldwell, G. A., Naider, F. and J. M. Becker, "Fungal lipopeptide mating pheromones: a model system for the study of protein prenylation," *Microbiol. Rev.* 59(3) :406–422, 1995.
5. Harborne, J. B., "Recent advances in the ecological chemistry of plant terpenoids," In: J. B. Harborne and F. A. Tomas-Barberan (eds.), Ecological Chemistry and Biochemistry of Plant Terpenoids. Clarendon Press, Oxford, p. 399–426, 1991.
6. Jorgensen, K., Ipsen, J. H., Mouritsen, O. G., Bennett, D. and M. J. Zuckermann, "The effects of density fluctuations on the partitioning of foreign molecules into lipid bilayers: Application to anaesthetics and insecticides," *Biochim. Biophys.* Acta. 1067:241–253, 1991.
7. Kadurugamuwa, J., Clarke, A. J. and T. J. Beveridge, "Surface action of gentamicin on *Pseudomonas aeruginosa*," *J. Bact.* 175(18):5798–5805, 1993.
8. Leclercq, R., Dutka-Malen, S., Brisson-Nöel, A., Molinas, C., Derlot, E., Arthur, M., Duval, J. and P. Courvalin, "Resistance of enterococci to aminoglycosides and glycopeptides," *Clin. Inf. Disease* 15:495–501, 1992.
9. Midoux, P., Mayer, R. and M. Monsigny, "Membrane permeabilization by α-helical peptides: a flow cytometry study," *Biochim. Biophys. Acta.* 1239:249–256, 1995.
10. Nikaido, H., "Prevention of drug access to bacterial targets: permeability barriers and active efflux," *Science* 264:382–388, 1994.
11. Parish, C. A and R. R. Rando, "Isoprenylation/ Methylation of proteins enhances membrane association by a hydrophobic mechanism," *Biochemistry* 35(26) :8473–8477, 1996.

We claim:

1. A method of promoting the uptake of exogenous antimicrobial compounds by bacterial cells comprising the step of exposing the bacterial cell to an amount of at least one sesquiterpenoid effective to enhance antimicrobial compound uptake in the bacterial cell and an antimicrobial compound, wherein the sesquiterpenoid is selected from the group consisting of farnesol, nerolidol, bisabolol and apritone.

2. The method of claim 1 wherein the sesquiterpenoid is nerolidol.

3. The method of claim 1 wherein the sesquiterpenoid is farnesol.

4. The method of claim 1 wherein the sesquiterpenoid is bisabolol.

5. The method of claim 1 wherein the sesquiterpenoid is apritone.

* * * * *

US006319958C1

(12) EX PARTE REEXAMINATION CERTIFICATE (5144th)
United States Patent
Johnson et al.

(10) Number: US 6,319,958 C1
(45) Certificate Issued: Jul. 12, 2005

(54) METHOD OF SENSITIZING MICROBIAL CELLS TO ANTIMICROBIAL COMPOUND

(75) Inventors: Eric A. Johnson, Madison, WI (US); Byron F. Brehm-Stecher, Madison, WI (US)

(73) Assignee: Wisconsin Alumni Research Foundation, Madison, WI (US)

Reexamination Request:
No. 90/007,035, May 10, 2004

Reexamination Certificate for:
Patent No.: 6,319,958
Issued: Nov. 20, 2001
Appl. No.: 09/102,466
Filed: Jun. 22, 1998

(51) Int. Cl.⁷ .............. A01N 31/00; C07C 35/00
(52) U.S. Cl. .............. 514/739; 514/675; 514/724; 568/875

(56) References Cited

U.S. PATENT DOCUMENTS 6,361,787 B1   3/2002   Shaheen et al.

*Primary Examiner*—Shengjun Wang

(57) ABSTRACT

A method of promoting the uptake of exogenous antimicrobial compounds by microbial cells is disclosed. In one embodiment, the method comprises the step of exposing the microbial cell to an amount of at least one sesquiterpenoid effective to enhance antimicrobial compound uptake in a microorganism and an antimicrobial compound. An antimicrobial composition comprising at least one sesquiterpenoid and an antimicrobial compound, the sesquiterpenoid being present in a concentration of between 0.1 mM and 50 mM, is also disclosed.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–5 is confirmed.

* * * * *